(12) United States Patent
Struble et al.

(10) Patent No.: US 7,058,450 B2
(45) Date of Patent: Jun. 6, 2006

(54) ORGANIZING DATA ACCORDING TO CARDIAC RHYTHM TYPE

(75) Inventors: Chester Struble, Eljsden (NL); Lambert Muhlenberg, Landgraaf (NL); Pierre Grandjean, Warsage (BE)

(73) Assignee: Medtronic, Inc., Minneapolis, MN (US)

( * ) Notice: Subject to any disclaimer, the term of this patent is extended or adjusted under 35 U.S.C. 154(b) by 360 days.

(21) Appl. No.: 10/126,816

(22) Filed: Apr. 22, 2002

(65) Prior Publication Data

US 2003/0199957 A1    Oct. 23, 2003

(51) Int. Cl.
  *A61N 1/365* (2006.01)
(52) U.S. Cl. .............. 607/18; 607/21; 607/23
(58) Field of Classification Search ........ 600/508–509, 600/513; 607/4–5, 9, 17, 21, 23, 123
  See application file for complete search history.

(56) References Cited

U.S. PATENT DOCUMENTS

| | | | |
|---|---|---|---|
| 3,857,399 A | 12/1974 | Zacouto | 607/9 |
| 4,316,472 A | 2/1982 | Mirowski et al. | 607/9 |
| 4,375,817 A | 3/1983 | Engle et al. | 607/4 |
| 4,379,439 A | 4/1983 | Stein | 119/57.6 |
| 4,384,585 A | 5/1983 | Zipes | 607/5 |
| 4,476,868 A | 10/1984 | Thompson | 607/14 |
| 4,556,063 A | 12/1985 | Thompson et al. | 607/32 |
| 4,577,633 A | 3/1986 | Berkovits et al. | 607/15 |
| 4,587,970 A | 5/1986 | Holley et al. | 607/15 |
| 4,726,380 A | 2/1988 | Vollmann | 607/15 |
| 4,727,877 A | 3/1988 | Kallok | 607/5 |
| 4,730,619 A | 3/1988 | Koning et al. | 607/23 |
| 4,800,005 A | 1/1989 | Pless et al. | 607/15 |
| 4,800,883 A | 1/1989 | Winstrom | 607/7 |
| 4,802,481 A | 2/1989 | Schroeppel | 607/24 |
| 4,821,723 A | 4/1989 | Baker et al. | 607/7 |
| 4,830,006 A | 5/1989 | Haluska et al. | 607/4 |
| 4,880,005 A | 11/1989 | Pless et al. | 607/15 |
| 4,928,688 A | 5/1990 | Mower | 607/9 |
| 4,949,719 A | 8/1990 | Pless et al. | 607/7 |
| 4,953,551 A | 9/1990 | Mehra et al. | 607/5 |
| 5,117,824 A | 6/1992 | Keimel et al. | 607/4 |
| 5,119,813 A | 6/1992 | Cohen | 607/23 |
| 5,131,388 A | 7/1992 | Pless et al. | 607/5 |
| 5,144,949 A | 9/1992 | Olson | 607/17 |
| 5,158,078 A | 10/1992 | Bennett et al. | 607/27 |
| 5,163,427 A | 11/1992 | Keimel | 607/5 |
| 5,188,105 A | 2/1993 | Keimel | 607/5 |
| 5,199,428 A | 4/1993 | Obel et al. | 607/44 |
| 5,207,218 A | 5/1993 | Carpentier et al. | 607/36 |

(Continued)

OTHER PUBLICATIONS

"Automatic Tachycardia Recognition" by Arzbaecher et al. PACE May-Jun. 1984, pp. 541-547.

*Primary Examiner*—Carl Layno
(74) *Attorney, Agent, or Firm*—Paul H. McDowall; Girma Wolde-Michael

(57) ABSTRACT

A plurality of sensors are disposed in and around the heart of a patient to collect data such as various electrical parameters, pressure parameters and temperature parameters. The data collected via the sensors may be organized and stored according to cardiac rhythm type. The organization of data according to cardiac rhythm type allows the patient's physician to be better able to monitor how the various parameters are related to the various cardiac rhythm types. In a typical embodiment, one or more of the sensors may be deployed on a single lead implanted in the heart.

12 Claims, 9 Drawing Sheets

U.S. PATENT DOCUMENTS

| | | | |
|---|---|---|---|
| 5,269,298 A | 12/1993 | Adams et al. | 607/5 |
| 5,312,453 A | 5/1994 | Shelton et al. | 607/19 |
| 5,314,430 A | 5/1994 | Bardy | 607/5 |
| 5,330,507 A | 7/1994 | Schwartz | 607/14 |
| 5,331,966 A | 7/1994 | Bennett et al. | 600/508 |
| 5,354,316 A | 10/1994 | Keimel | 607/15 |
| 5,533,511 A * | 7/1996 | Kaspari et al. | 600/485 |
| 5,540,727 A | 7/1996 | Tockman et al. | 607/18 |
| 5,545,186 A | 8/1996 | Olson | 607/14 |
| 5,584,868 A | 12/1996 | Salo et al. | 607/17 |
| 5,626,623 A | 5/1997 | Kieval et al. | 607/23 |
| 5,728,140 A | 3/1998 | Salo et al. | 607/9 |
| 5,755,736 A * | 5/1998 | Gillberg et al. | 607/4 |
| 5,800,465 A | 9/1998 | Thompson | 607/9 |
| 6,021,350 A | 2/2000 | Mathson | 607/17 |
| 6,148,233 A * | 11/2000 | Owen et al. | 607/5 |
| 6,304,773 B1 * | 10/2001 | Taylor et al. | 600/515 |
| 6,567,700 B1 * | 5/2003 | Turcott et al. | 607/9 |
| 2003/0045910 A1 * | 3/2003 | Sorensen et al. | 607/23 |

* cited by examiner

| | Sinus Rhythm | BiVDD Paced | SVT | PVC | VT | PAF Paced |
|---|---|---|---|---|---|---|
| RV Systolic Pressure | | | | | | |
| RV Diastolic Pressure | | | | | | |
| RV Mean Pressure | | | | | | |
| +dP/dt | | | | | | |
| -dP/dt | | | | | | |
| ePAD | | | | | | |
| Pulse Pressure | | | | | | |
| STI | | | | | | |
| PEI | | | | | | |
| Heart Rate | | | | | | |
| Patient Activity | | | | | | |
| Patient Temp. | | | | | | |
| Oxygen Saturation | | | | | | |

FIG. 8

ORGANIZING DATA ACCORDING TO
CARDIAC RHYTHM TYPE

FIELD OF THE INVENTION

The invention relates to implantable medical devices, and more particularly, to medical devices that monitor or regulate cardiac functions.

BACKGROUND

Many patients that suffer from congestive heart failure (CHF) develop a wide QRS complex resulting from a delayed activation of one of the ventricles in the heart, and inter-and/or intraventricular electro-mechanical dysynchrony. This ventricular "dysynchrony" may be caused by dilation of the heart, which disrupts the conductive pathways and interferes with depolarization sequences. Ventricular dysynchrony may worsen heart failure symptoms.

In a classic case of ventricular dysynchrony, the patient's right ventricle activates first, and the left ventricle activates at a later time. The patient often experiences a reduction in cardiac output because the ventricles begin contraction at significantly different times. The timing imbalance may also cause the patient to experience paradoxical septal motion, mitral regurgitation or decreased ventricular filling time.

Patients having a wide QRS complex or having inter-and/or intraventricular electro-mechanical dysynchrony may receive benefits from an implanted medical device, such as a pacemaker, that paces both ventricles. The implanted medical device senses or paces atrial contractions, waits a predetermined time (or atrioventricular (AV) delay) after each sensed or paced atrial contraction, and then paces both ventricles. The ventricles may be paced simultaneously, or one ventricle may be paced before another. This bi-ventricular pacing is one form of cardiac resynchronization, and it provides many CHF patients with improvements in quality of life, exercise capacity and overall cardiac function.

Generally speaking, cardiac resynchronization refers to pacing therapies applied by implanted medical devices with pacing leads in two or more complementary chambers of the heart, i.e., the atria or the ventricles. In response to a sensed or paced event, the pacemaker delivers pacing pulses or stimulations to two complementary chambers of the heart. The pacing pulses may be, but need not be, delivered simultaneously.

Many pacemakers, including pacemakers that provide cardiac resynchronization, may monitor cardiac rhythms for various forms of arrhythmia. In general, when a pacemaker senses a potential arrhythmia, the pacemaker may execute specialized classification algorithms. In this way, the pacemaker can discriminate between or among various heart rhythms and can classify arrhythmias according to type.

In some patients, such as patients that receive multiple-chamber pacing, several sensors may be implanted in or around the patient's heart. In addition to the pacing electrodes of the pacemaker, which also sense electrical activity, the patient may receive one or more sensors that respond to other conditions. For example, the patient may receive a pressure sensor. A pressure sensor may be useful in monitoring conditions that may accompany heart failure, such as cardiac decompensation.

Multiple-chamber pacing systems in general, and bi-ventricular and bi-atrial pacing systems in particular, are known in the art. Techniques for classification of various arrhythmias are likewise known in the art. In addition, use of sensors such as pressure sensors, including use of pressure sensors with multiple-chamber pacing systems, is also known in the art. There is a need, however, for useful coordination of these techniques. In addition, some of these techniques may involve implantation of multiple electrodes or other sensors, which can be difficult and time-consuming.

Examples of these techniques and/or devices may be found in the issued U.S. Patents listed in Table 1 below.

TABLE 1

| U.S. Pat. No. | Inventor | Issue Date |
| --- | --- | --- |
| 3,857,399 | Zacouto | Dec. 31, 1974 |
| 4,730,619 | Koning et al. | Mar. 15, 1988 |
| 4,802,481 | Schroeppel | Feb. 07, 1989 |
| 4,928,688 | Mower | May 29, 1990 |
| 5,119,813 | Cohen | Jun. 09, 1992 |
| 5,540,727 | Tockman et al. | Jul. 30, 1996 |
| 5,584,868 | Salo et al. | Dec. 17, 1996 |
| 5,626,623 | Kieval et al. | May 06, 1997 |
| 5,728,140 | Salo et al. | Mar. 17, 1998 |
| 6,021,350 | Mathson | Feb. 01, 2000 |

All patents listed in Table 1 above are hereby incorporated by reference herein in their respective entireties. As those of ordinary skill in the art will appreciate readily upon reading the Summary of the Invention, Detailed Description of the Preferred Embodiments and claims set forth below, many of the devices and methods disclosed in the patents of Table 1 may be modified advantageously by using the techniques of the present invention.

SUMMARY OF THE INVENTION

The present invention has certain objects. That is, various embodiments of the present invention provide solutions to one or more problems existing in the prior art with respect to pacemakers, including multiple-chamber cardiac pacemakers in general and bi-ventricular cardiac pacemakers in particular. These problems include, for example, an inability to use classification techniques to organize data such as various pressure-related parameters. Various embodiments of the present invention have the object of solving at least one of the foregoing problems.

It is an object of the invention to collect data about a variety of parameters. Many of these parameters may be pressure-related, but the invention is not limited to pressure-related parameters. Data may also be collected pertaining to parameters such as patient temperature, patient activity and oxygen saturation. These parameters may be affected by the patient's cardiac rhythm type. It is another object of the invention to organize the data so that the patient's physician can monitor how the parameters are affected by the patient's cardiac rhythm type. The organized data may be used by the patient's physician to monitor the patient's condition and the patient's therapy. The data may also be used to automatically adjust the patient's therapy. Certain pressure parameters observed during bi-ventricular pacing, for example, may be used to gauge the effectiveness of the bi-ventricular pacing. The parameters may also be used to adjust one or more timing intervals to improve the effectiveness of the pacing, for example.

To collect the data, many sensors may be placed in and around the patient's heart. In addition to pacing and sensing electrodes, for example, sensors such as pressure sensors, temperature sensors and oxygen sensors may be placed in and around the heart. It is an additional object of the invention to reduce the practical difficulties associated with implantation of sensors. In particular, many of the sensors may be placed upon a single lead, thereby reducing the amount of material implanted in the patient and simplifying the implantation process. In one embodiment of the invention, the single lead descends into the patient's right ventricle and is implanted within the interventricular septum. In this way, several sensors, including right and left ventricular sensing and pacing electrodes, may be deployed with a single implantation.

Various embodiments of the invention may possess one or more features capable of fulfilling the above objects. In general, the invention includes a pacemaker. In many cases, the pacemaker provides multi-chamber pacing, and may provide pacing stimuli to both ventricles of the heart, and may provide pacing stimuli to one or both atria as well. The invention may also include sensors that collect pressure data, temperature data or other data from cardiac chambers such as the right ventricle, the left ventricle or both ventricles. Many parameters can be measured, observed or derived from data such as pressure data, and many of these parameters may have clinical significance.

The invention also includes a processor that can detect and classify various types of cardiac rhythms. The data collected by the sensors may vary when heart rhythm changes. Pressure data collected during an episode of ventricular tachycardia, for example, may be significantly different from pressure data collected during an unpaced sinus rhythm.

The invention organizes the collected data according to cardiac rhythm type. This organization may be helpful in monitoring and providing therapy for the patient. Data collected during bi-ventricular pacing, for example, will not be commingled with data collected during an episode of arrhythmia. As a result, detailed evaluation of the collected data may be performed. Data that suggest successful bi-ventricular pacing, for example, will not be corrupted by commingling with atypical data caused by atypical cardiac rhythms.

The invention may offer one or more advantages, including enhanced monitoring of the status of the patient. By organizing the data according to cardiac rhythm type, the patient's physician may be better able to monitor how the various parameters are related to the various cardiac rhythm types. These advantages may be realized in a variety of one-, two-, three-, and four-chamber implantable devices.

A single-lead embodiment of the invention, in which multiple sensors are carried on a common lead, may be advantageous because it allows for collection of the data with fewer implantation complications. The invention is not limited to use with a single lead, but a single lead can greatly simplify the implantation and data collection processes.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIG. 8 is a chart showing one technique for organizing data according to cardiac rhythm type.

DETAILED DESCRIPTION OF THE PREFERRED EMBODIMENTS

In the following detailed description of the preferred embodiments, reference is made to the accompanying drawings that form a part hereof, and in which are shown by way of illustration specific embodiments in which the invention may be practiced. It is to be understood that other embodiments may be utilized and structural or logical changes may be made without departing from the scope of the present invention. The following detailed description, therefore, is not to be taken in a limiting sense, and the scope of the present invention is defined by the appended claims.

Figure 1:
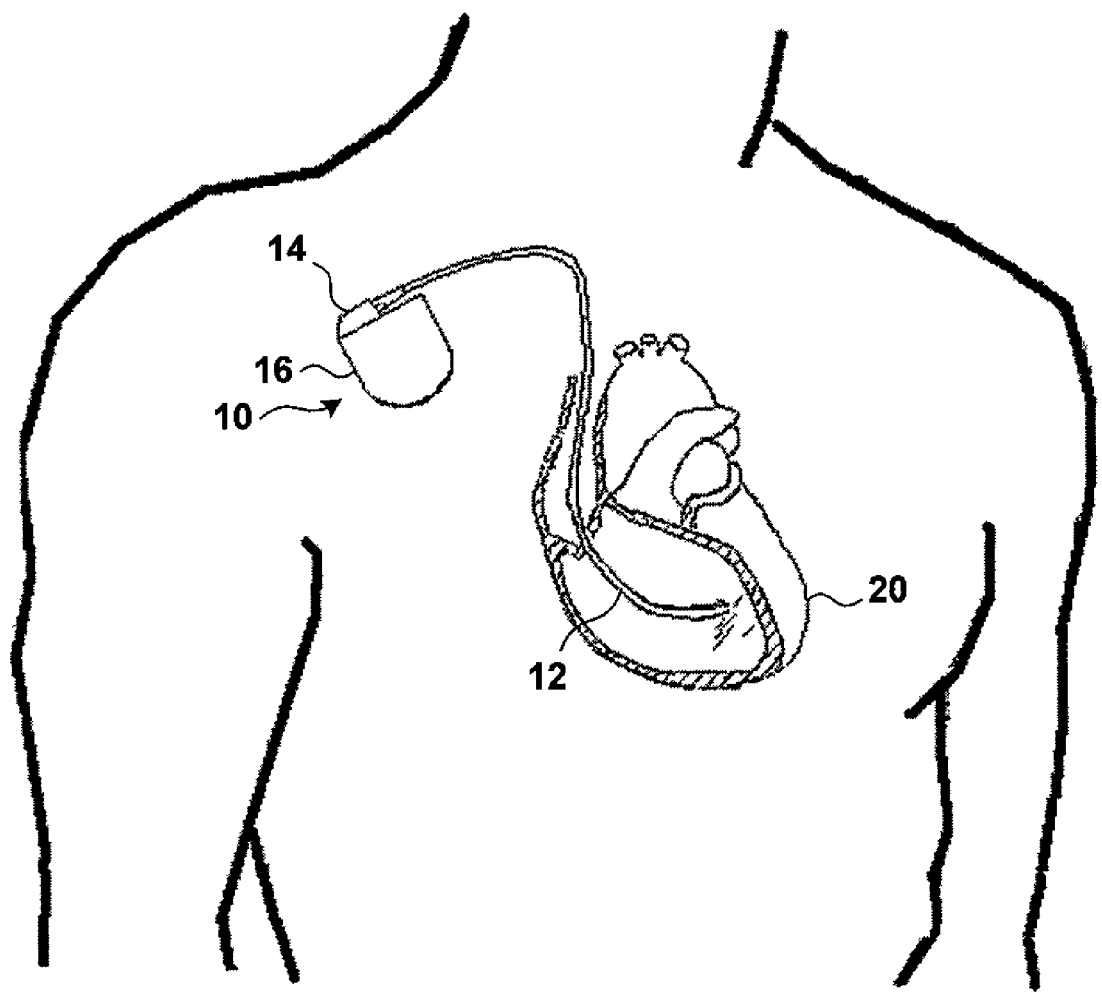
FIG. 1 is a schematic view of an exemplary implantable medical device.

FIG. 1 is a simplified schematic view of one embodiment of implantable medical device ("IMD") 10 of the present invention. IMD 10 shown in FIG. 1 is a pacemaker comprising at least one pacing and sensing lead 12 attached to connector module 14 of hermetically sealed enclosure 16 and implanted near human or mammalian heart 20. Pacing and sensing lead 12 senses electrical signals attendant to the depolarization and repolarization of the heart 20, and further provides pacing pulses for causing depolarization of cardiac tissue in the vicinity of electrodes disposed on the distal ends thereof. Lead 12 may have unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al., or U.S. Pat. No. 5,144,949 to Olson, all hereby incorporated by reference herein, each in its respective entirety.

Figure 2:
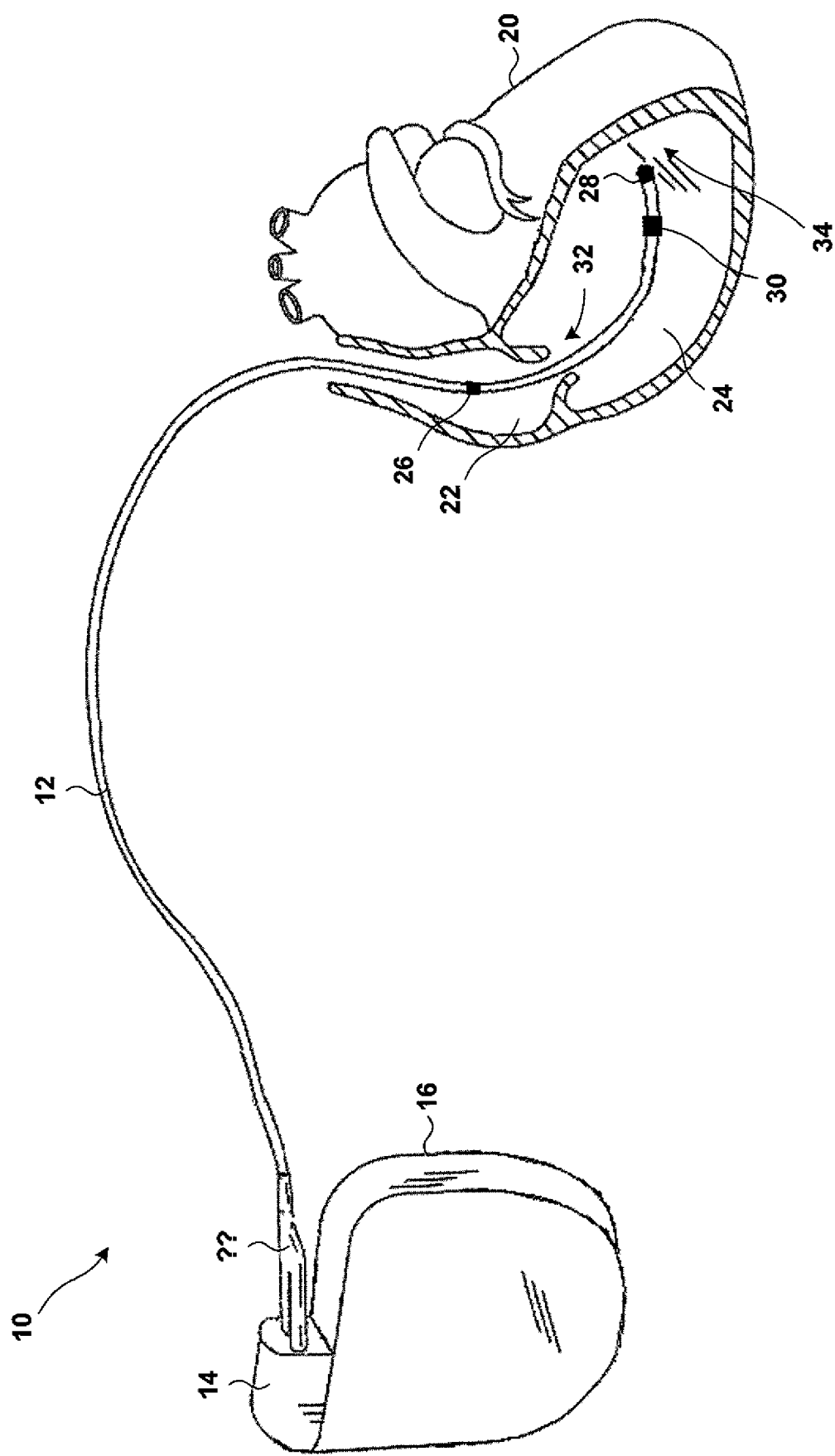
FIG. 2 shows the exemplary implantable medical device of FIG. 1 located in and near a heart.

FIG. 2 shows connector module 14 and hermetically sealed enclosure 16 of IMD 10 located in and near human or mammalian heart 20. In FIG. 2, a single lead 12 extends from connector module 14 to the right atrium 22 and right ventricle 24, respectively, of heart 20. An atrial electrode 26 is disposed near the distal end of lead 12 and is located in right atrium 22. One or more ventricular electrodes are disposed at the distal end of lead 12. The right ventricular electrode 28 is located in right ventricle 24. A left ventricular electrode (not shown in FIG. 2) may also be disposed at the distal end of lead 12, as will be described below.

Further, a pressure sensor 30 may be disposed near the distal end of lead 12. In FIG. 2, pressure sensor 30 is disposed in right ventricle 24. In a typical embodiment, pressure sensor 30 responds to the absolute pressure inside right ventricle 24, and may be, for example, a capacitive or piezoelectric absolute pressure sensor.

Lead 12 descends through right atrium 22, descends through right atrioventricular valve 32 into right ventricle 24, and is implanted within the interventricular septum 34.

In this way, one or more sensing and pacing electrodes and one or more pressure sensors can be disposed at selected sites in heart 20 through placement of a single lead 12.

Electrodes 26, 28 may sense the activity of the right atrium or right ventricle. Right ventricular electrode 28 may also deliver a stimulus. Although right atrial electrode 26 may also be configured to deliver a stimulus, electrode 26 is unlikely in practice to be located at a site in right atrium at which an effective pacing stimulus may be delivered. Accordingly, it will be assumed that right atrial electrode 26 principally senses atrial activity and does not deliver pacing stimuli. The invention encompasses embodiments in which right atrial electrode 26 is configured to deliver a stimulus, however, as well as embodiments in which right atrial electrode 26 is not configured to deliver a stimulus.

Figure 3:
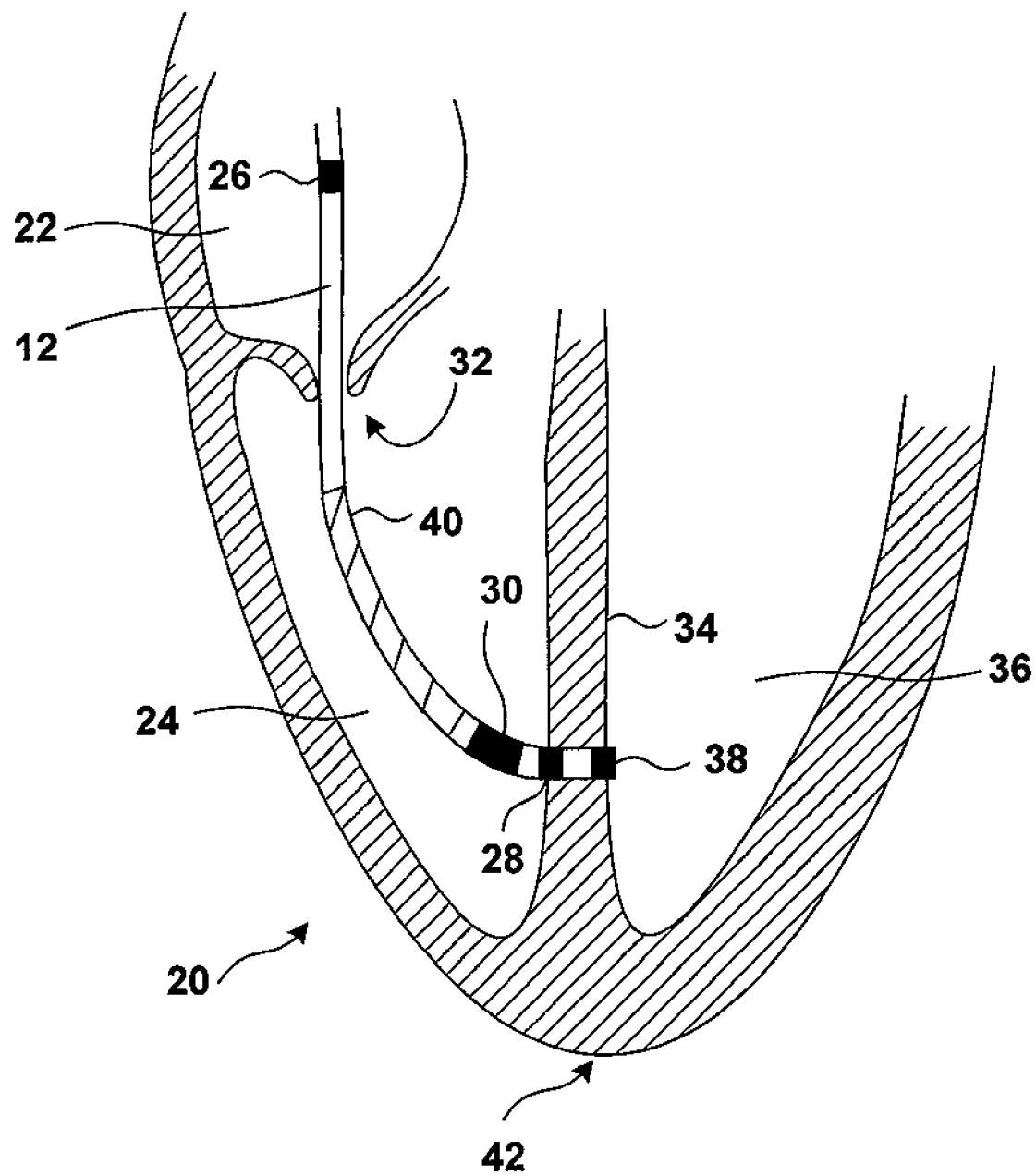
FIG. 3 shows a frontal cross-section of the heart with an exemplary lead.

FIG. 3 shows a cross-section of heart 20. As in FIG. 2, lead 12 descends through right atrium 22, descends through right atrioventricular valve 32 into right ventricle 24, and is implanted within the interventricular septum 34. In FIG. 3, lead 12 penetrates into left ventricle 36. Left ventricular electrode 38 at the distal tip of lead 12 is thereby disposed in left ventricle 36. Like right ventricular lead 28, left ventricular electrode 38 may sense electrical signals attendant to the depolarization and repolarization of heart 20, and may deliver pacing pulses to cause depolarization of cardiac tissue.

Lead 12 may further include a defibrillation electrode 40. Defibrillation electrode 40 may be fabricated from platinum, platinum alloy or other materials known to be usable in implantable defibrillation electrodes and may be about 5 cm in length.

Implantation of lead 12 in septum 34 may be realized using any of a number of techniques. For example, when lead 12 is first threaded into heart 20, lead 12 may be surrounded by a puncture needle. A guiding catheter can be used to guide lead 12 and the puncture needle to the desired location within heart 20. In this case, the guiding catheter may guide lead 12 and the puncture needle to interventricular septum 34, superior to the apex 42.

Once the guiding catheter has guided lead 12 and the puncture needle to interventricular septum 34, the puncture needle may be used to puncture interventricular septum 34. The puncture needle may be retracted, and lead 12 can be positioned within interventricular septum 34 such that left ventricular electrode 38 is in close proximity to left ventricle 36.

The implantation shown in FIG. 3 is merely for illustration, and the invention is not limited to the particular implantation site shown. The point of penetration through septum 34, for example, may be closer to or further from apex 42 than is shown. In addition, the invention encompasses implantations in which septum 34 is not fully penetrated. Furthermore, the pressure sensor, with or without one or more pacing electrodes, need not be implanted in septum 34. The pressure sensor may be implanted using, for example, a trans-epicardial to myocardial to endocardium approach.

Moreover, the arrangement of electrodes and pressure sensors in FIG. 3 is merely for illustration. Defibrillation electrode 40, for example, may be located more distally than is shown in FIG. 3. In some embodiments of the invention, defibrillation electrode 40 may be omitted in its entirety.

Furthermore, atrial lead 26, right ventricular lead 28 and left ventricular electrode 38 are depicted as unipolar electrodes, but may be realized as bipolar electrodes or as any combination of bipolar and unipolar electrodes. In a typical embodiment, the electrodes may be ring electrodes coated with steroid such as dexamethasone to reduce fibrous growth around the electrodes and to reduce inflammation. More or fewer electrodes and/or pressure sensors may be disposed on lead 12 than are shown in FIG. 3. The invention is not limited to the arrangement of electrodes and pressure sensors shown in FIG. 3.

Figure 4:
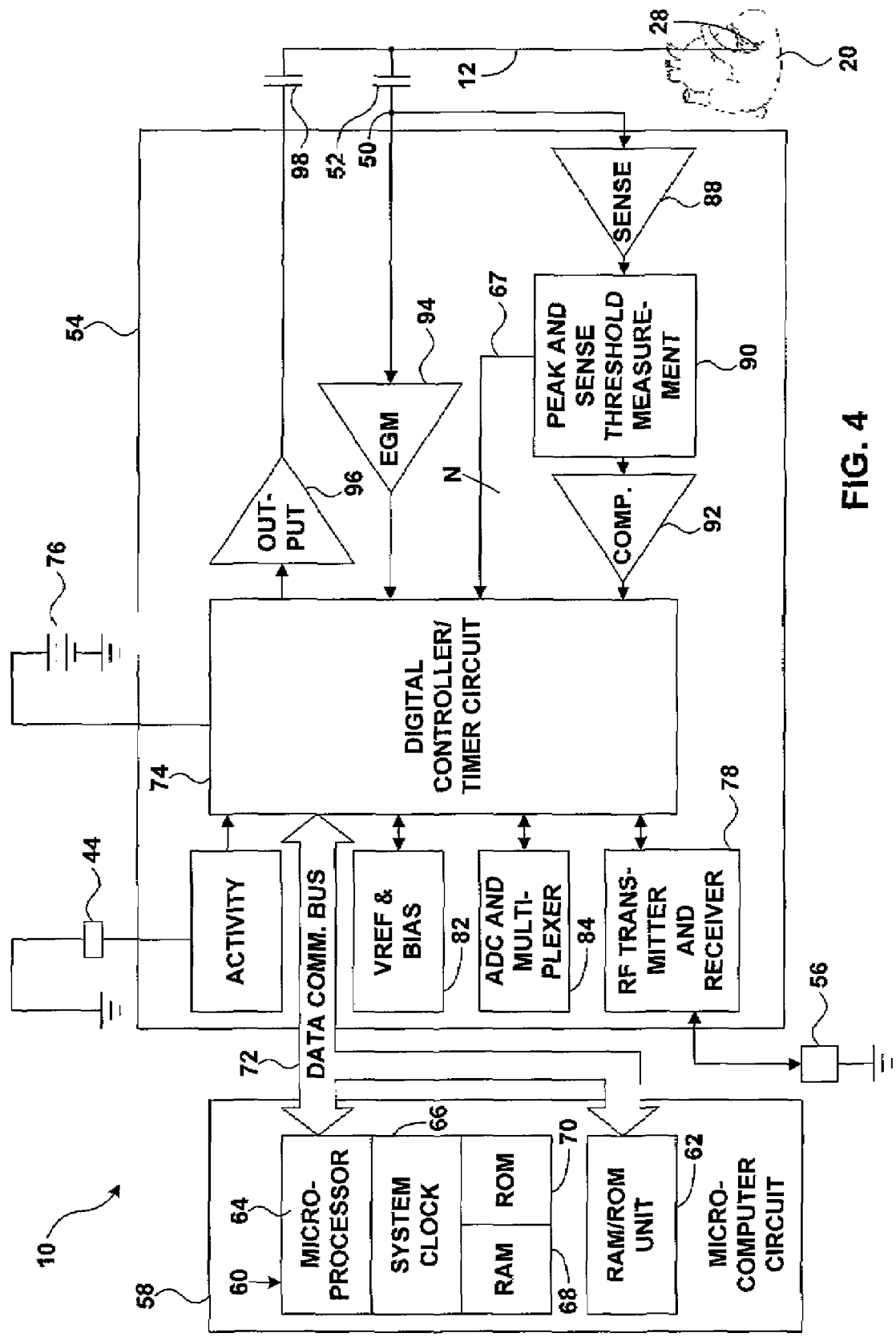
FIG. 4 is a block diagram illustrating the constituent components of the implantable medical device of FIGS. 1, 2 and 3.

FIG. 4 shows a block diagram illustrating the constituent components of IMD 10 in accordance with one embodiment of the present invention, where IMD 10 is a pacemaker having a microprocessor-based architecture. IMD 10 is shown as including activity sensor or accelerometer 44, which is preferably a piezoceramic accelerometer bonded to a hybrid circuit located inside enclosure 16 (shown in FIGS. 1 and 2 ). Activity sensor 44 typically (although not necessarily) provides a sensor output that varies as a function of a measured parameter relating to a patient's metabolic requirements. IMD 10 in FIG. 4 is shown with lead 12 connected thereto, by which one of the electrodes, such as right ventricular electrode 28, is coupled to IMD 10. However, it is understood that similar circuitry and connections not explicitly shown in FIG. 4 may apply to electrodes such as left ventricular electrode 38 and atrial electrode 26 (shown in FIG. 3).

IMD 10 in FIG. 4 is most preferably programmable by means of an external programming unit (not shown in the figures). One such programmer is the commercially available Medtronic Model 9790 programmer, which is microprocessor-based and provides a series of encoded signals to IMD 10, typically through a programming head which transmits or telemeters radio-frequency (RF) encoded signals to IMD 10. Such a telemetry system is described in U.S. Pat. No. 5,312,453 to Wyborny et al., hereby incorporated by reference herein in its entirety. The programming methodology disclosed in Wyborny et al.'s '453 patent is identified herein for illustrative purposes only. Any of a number of suitable programming and telemetry methodologies known in the art may be employed so long as the desired information is transmitted to and from the pacemaker.

As shown in FIG. 4, lead 12 is coupled to node 50 in IMD 10 through input capacitor 52. Activity sensor or accelerometer 44 is most preferably attached to a hybrid circuit located inside hermetically sealed enclosure 16 of IMD 10. The output signal provided by activity sensor 44 is coupled to input/output circuit 54. Input/output circuit 54 contains analog circuits for interfacing with heart 20, activity sensor 44, antenna 56 and circuits for the application of stimulating pulses to heart 20. The rate of heart 20 is controlled by software-implemented algorithms stored within microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference herein in its entirety. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 4 are powered by an appropriate implantable battery power source 76 in accordance with common practice in the art. For the sake of clarity, the coupling of battery power to the various components of IMD 10 is not shown in the figures.

Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063 issued to Thompson et al., hereby incorporated by reference herein in its entirety, or to that disclosed in the above-referenced '453 patent to Wyborny et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 4, VREF and bias circuit 82 most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled from microprocessor 64 via data bus 72 to digital controller/timer circuit 74, where digital timers and counters establish the overall escape interval of the IMD 10 as well as various refractory, blanking and other timing windows for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by electrode 28. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is also provided to comparator/threshold detector 92. By way of example, sense amplifier 88 may correspond to that disclosed in U.S. Pat. No. 4,379,459 to Stein, hereby incorporated by reference herein in its entirety.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides amplified pacing stimuli to patient's heart 20 through coupling capacitor 98 in response to a pacing trigger signal provided by digital controller/timer circuit 74 each time either (a) the escape interval times out, (b) an externally transmitted pacing command is received, or (c) in response to other stored commands as is well known in the pacing art. By way of example, output amplifier 96 may correspond generally to an output amplifier disclosed in U.S. Pat. No. 4,476,868 to Thompson, hereby incorporated by reference herein in its entirety.

The specific embodiments of sense amplifier 88, output pulse generator 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 20.

In some preferred embodiments of the present invention, IMD 10 may operate in various non-rate-responsive modes, including, but not limited to, DDD, DDI, VVI, VOO and VVT modes. In other preferred embodiments of the present invention, IMD 10 may operate in various rate-responsive modes, including, but not limited to, DDDR, DDIR, VVIR, VOOR and VVTR modes. Some embodiments of the present invention are capable of operating in both non-rate-responsive and rate responsive modes. Moreover, in various embodiments of the present invention IMD 10 may be programmably configured to operate so that it varies the rate at which it delivers stimulating pulses to heart 20 in response to one or more selected sensor outputs being generated. Numerous pacemaker features and functions not explicitly mentioned herein may be incorporated into IMD 10 while remaining within the scope of the present invention.

The present invention is not limited in scope to single-sensor or dual-sensor pacemakers, and is not limited to IMD's comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with one or more leads or with multiple-chamber pacemakers, for example. At least some embodiments of the present invention may be applied equally well in the contexts of single-, dual-, triple- or quadruple-chamber pacemakers or other types of IMD's. See, for example, U.S. Pat. No. 5,800,465 to Thompson et al., hereby incorporated by reference herein in its entirety, as are all U.S. Patents referenced therein.

IMD 10 may also be a pacemaker-cardioverter-defibrillator ("PCD") corresponding to any of numerous commercially available implantable PCD's. Various embodiments of the present invention may be practiced in conjunction with PCD's such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless, and U.S. Pat. No. 4,821,723 to Baker et al., all hereby incorporated by reference herein, each in its respective entirety.

Figure 5:
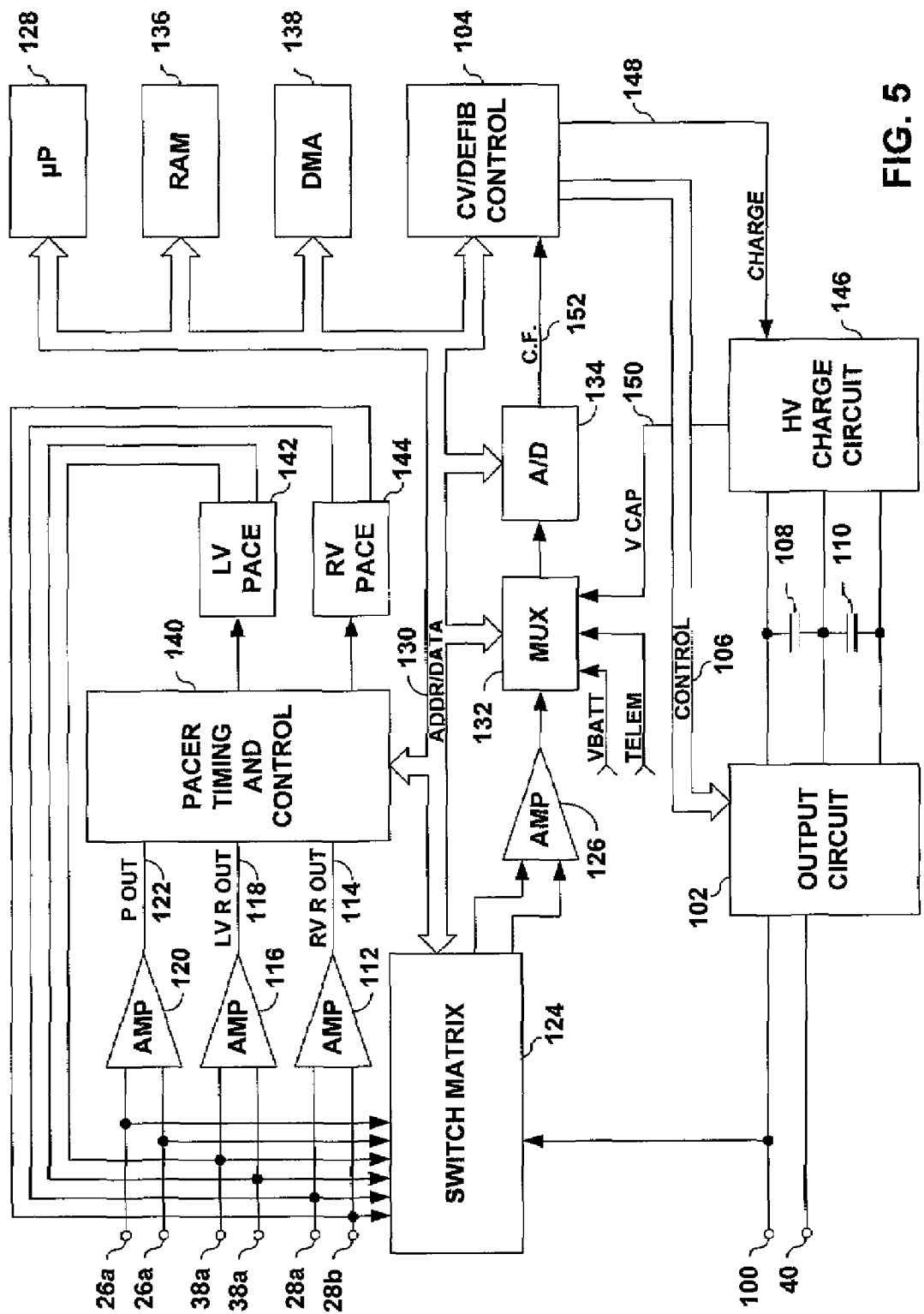
FIG. 5 is a functional schematic diagram of the embodiment of an implantable medical device shown in FIGS. 1, 2 and 3.

FIG. 5 is a functional schematic diagram of one embodiment of IMD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

IMD 10 is provided with an electrode system. Electrode 100 in FIG. 5 includes the uninsulated portion of enclosure 16 of IMD 10. Electrodes 40 and 100 are coupled to high voltage output circuit 102, which includes high voltage switches controlled by CV/defib control logic 104 via control bus 106. Switches disposed within circuit 102 determine which electrodes are employed and which electrodes are coupled to the positive and negative terminals of a capacitor bank (which includes capacitors 108 and 110) during delivery of defibrillation pulses.

Electrode 28 is represented in FIG. 5 by bipolar electrodes 28a and 28b, which are located in right ventricle 24 of the patient and are coupled to the R-wave amplifier 112, which preferably takes the form of an automatic gain controlled amplifier providing an adjustable sensing threshold as a function of the measured R-wave amplitude. A signal is generated on right ventricular (RV) R-out line 114 whenever the signal sensed between electrodes 28a and 28b exceeds the present sensing threshold.

Electrode 38 is represented in FIG. 5 as by bipolar electrodes 38a and 38b, which are located in or proximate to left ventricle 36. Electrodes 38a and 38b are coupled to the R-wave amplifier 116, which preferably takes the form of an automatic gain controlled amplifier providing an adjustable sensing threshold as a function of the measured R-wave amplitude. A signal is generated on left ventricular (LV) R-out line 118 whenever the signal sensed between electrodes 38a and 38b exceeds the present sensing threshold.

Electrode 26 is represented in FIG. 5 as by bipolar electrodes 26a and 26b, which are located in right atrium 22. Electrodes 26a and 26b are coupled to the P-wave amplifier 120, which preferably also takes the form of an automatic gain controlled amplifier providing an adjustable sensing threshold as a function of the measured P-wave amplitude. A signal is generated on P-out line 122 whenever the signal sensed between electrodes 26a and 26b exceeds the present sensing threshold. The general operation of R-wave and P-wave amplifiers 112, 116 and 120 may correspond to that disclosed in U.S. Pat. No. 5,117,824 to Keimel et al., hereby incorporated by reference herein in its entirety.

Switch matrix 124 is used to select which of the available electrodes are coupled to wide band (0.5–200 Hz) amplifier 126 for use in digital signal analysis. Selection of electrodes is controlled by microprocessor 128 via data/address bus 130, which selections may be varied as desired. Signals from the electrodes selected for coupling to bandpass amplifier 126 are provided to multiplexer 132, and thereafter converted to multi-bit digital signals by A/D converter 134, for storage in random access memory 136 under control of direct memory access circuit 138. Microprocessor 128 may employ digital signal analysis techniques to characterize the digitized signals stored in random access memory 136 to recognize and classify the patient's heart rhythm employing any of the numerous signal processing methodologies known to the art. Some examples of classification will be described below.

The remainder of the circuitry is dedicated to the provision of cardiac pacing, cardioversion and defibrillation therapies, and, for purposes of the present invention may correspond to circuitry known to those skilled in the art. The following exemplary apparatus is disclosed for accomplishing pacing, cardioversion and defibrillation functions. Pacer timing/control circuitry 140 preferably includes programmable digital counters which control the basic time intervals associated with DDD, VVI, DVI, VDD, AAI, DDI and other modes of single- and dual-chamber pacing well known to the art. Circuitry 140 also preferably controls escape intervals associated with anti-tachyarrhythmia pacing in both the atrium and the ventricle, employing any anti-tachyarrhythmia pacing therapies known to the art. In addition, circuitry 140 may control the atrioventricular delay that separates a sensed or paced atrial event from a paced ventricular event, and/or the V1–V2 interval that separates a pace of one ventricle during a cardiac cycle from a pace of the complementary ventricle during the cardiac cycle.

Intervals defined by pacing circuitry 140 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 128, in response to stored data in memory 136 and are communicated to pacing circuitry 140 via address/data bus 132. Pacer circuitry 140 also determines the amplitude of the cardiac pacing pulses under control of microprocessor 128.

During pacing, escape interval counters within pacer timing/control circuitry 140 are reset upon sensing of R-waves and P-waves as indicated by a signals on lines 114, 118 and 122, and in accordance with the selected mode of pacing on time-out trigger generation of pacing pulses by pacer output circuitry 142 and 144, which are coupled to electrodes 28a, 28b, 38a and 38b. In the embodiment shown in FIG. 5, atrial electrodes 26a and 26b are configured for sensing electrical signals attendant to the depolarization and repolarization of heart 20, but not for delivering pacing pulses. Accordingly, no pacer output circuitry is coupled to atrial electrodes 26a and 26b.

Escape interval counters are also reset on generation of pacing pulses and thereby control the basic timing of cardiac pacing functions, including anti-tachyarrhythmia pacing. The durations of the intervals defined by escape interval timers are determined by microprocessor 128 via data/address bus 132. The value of the count present in the escape interval counters when reset by sensed R-waves and P-waves may be used to measure the durations of R—R intervals, P—P intervals, P-R intervals and R-P intervals, which measurements are stored in memory 136 and used to detect the presence of tachyarrhythmias.

Microprocessor 128 most preferably operates as an interrupt driven device, and is responsive to interrupts from pacer timing/control circuitry 140 corresponding to the occurrence of sensed P-waves and R-waves and corresponding to the generation of cardiac pacing pulses. Those interrupts are provided via data/address bus 130. Any necessary mathematical calculations to be performed by microprocessor 128 and any updating of the values or intervals controlled by pacer timing/control circuitry 140 take place following such interrupts.

Detection of atrial or ventricular tachyarrhythmias, as employed in the present invention, may correspond to tachyarrhythmia detection algorithms known in the art. For example, the presence of an atrial or ventricular tachyarrhythmia may be confirmed by detecting a sustained series of short R—R or P—P intervals of an average rate indicative of tachyarrhythmia or an unbroken series of short R—R or P—P intervals. The rate of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005 issued to Pless et al., and U.S. Pat. No. 4,830,006 issued to Haluska et al., all incorporated by reference herein, each in its respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pages 167–170, also incorporated by reference herein in its entirety. Atrial fibrillation detection methodologies are disclosed in Published PCT Application Ser. No. US92/02829, Publication No. WO92/8198, by Adams et al., and in the article "Automatic Tachycardia Recognition," by Arzbaecher et al., published in PACE, May-June, 1984, pp. 541–547, both of which are incorporated by reference herein in their entireties.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 128 into the pacer timing and control circuitry 140, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al., U.S. Pat. No. 4,880,005, issued to Pless et al., U.S. Pat. No. 4,726,380, issued to Vollmann et al., and U.S. Pat. No. 4,587,970, issued to Holley et al., all of which are incorporated herein by reference in their entireties, may also be employed.

In the event that generation of a cardioversion or defibrillation pulse is required, microprocessor 128 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 128 activates cardioversion/defibrillation control circuitry 104, which initiates charging of high voltage capacitors 108 and 110 via charging circuit 146, under the control of high voltage charging control line 148. The voltage on the high voltage capacitors is monitored via VCAP line 150, which is passed through multiplexer 132 and in response to reaching a predetermined value set by microprocessor 128, results in generation of a logic signal on Cap Full (CF) line 152 to terminate charging. Thereafter, timing of the delivery of the defibrillation or cardioversion pulse is controlled by pacer timing/control circuitry 140. Following delivery of the fibrillation or tachycardia therapy, microprocessor 128 returns the device to cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al., and U.S. Pat. No. 4,316,472 to Mirowski et al., hereby incorporated by reference herein, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all hereby incorporated by reference herein in their entireties, may also be employed.

Continuing to refer to FIG. 5, delivery of cardioversion or defibrillation pulses is accomplished by output circuit 102 under the control of control circuitry 104 via control bus 106. Output circuit 102 determines whether a monophasic or biphasic pulse is delivered, the polarity of the electrodes and which electrodes are involved in delivery of the pulse. Output circuit 102 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the above-cited patent issued to Mehra and in U.S. Pat. No. 4,727,877 to Kallok, hereby incorporated by reference herein in its entirety.

An example of circuitry which may be used to control delivery of monophasic pulses is disclosed in U.S. Pat. No. 5,163,427 to Keimel, also incorporated by reference herein in its entirety. Output control circuitry similar to that disclosed in U.S. Pat. No. 4,953,551 to Mehra et al. or U.S. Pat. No. 4,800,883 to Winstrom, both incorporated by reference herein in their entireties, may also be used in conjunction with various embodiments of the present invention to deliver biphasic pulses.

Alternatively, IMD 10 may be an implantable nerve stimulator or muscle stimulator such as that disclosed in U.S. Pat. No. 5,199,428 to Obel et al., U.S. Pat. No. 5,207,218 to Carpentier et al., or U.S. Pat. No. 5,330,507 to Schwartz, or an implantable monitoring device such as that disclosed in U.S. Pat. No. 5,331,966 issued to Bennet et al., all of which are hereby incorporated by reference herein, each in its respective entirety. The present invention is believed to find wide application to any form of implantable electrical device for use in conjunction with electrical leads.

Figure 6:
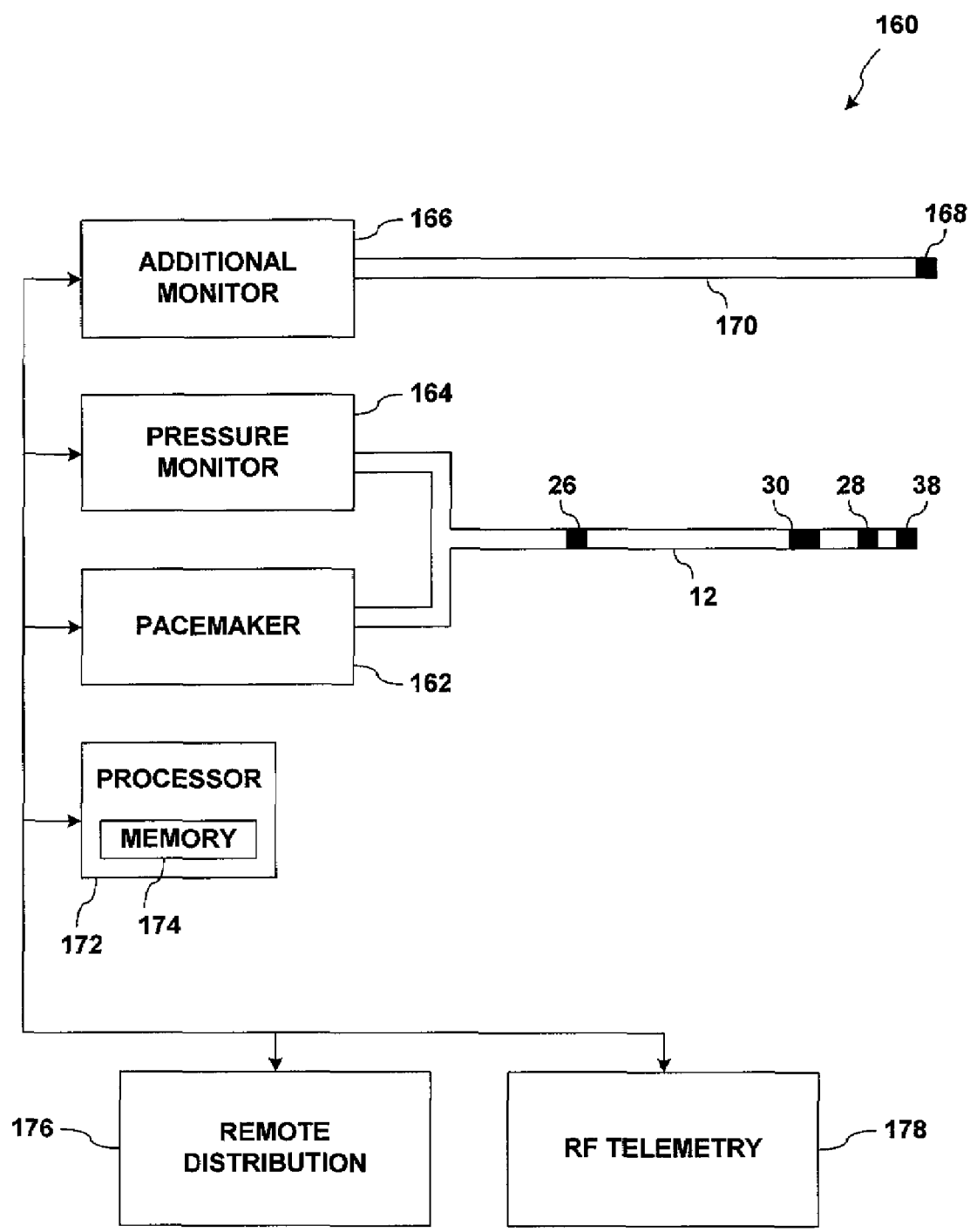
FIG. 6 is a diagram of a system including a pressure monitor, a cardiac pacemaker and an additional monitor.

FIG. 6 shows a system 160 illustrating an embodiment of the invention. System 160, which may be implantable in a human being or a mammal, may include a cardiac pacemaker 162. Pacemaker 162 may pace one or more chambers of heart 20 (not shown in FIG. 6) using one or more pacing modes. Pacemaker 162 may be, for example, a device that senses and paces the right and left sides of heart 20 as shown in FIGS. 1–5. The invention is not limited to the exemplary pacemakers shown in FIGS. 1–5, however. In some embodiments, a heart monitor (not shown in FIG. 6) may supplant pacemaker 162, and may be capable of sensing cardiac activity but not delivering pacing stimuli.

Pacemaker 162 may be one of the many forms of implantable medical devices 10 described above, or may be an external pacemaker. Lead 12 is coupled to pacemaker 162. Atrial electrode 26, right ventricular electrode 28, left ventricular electrode 38 and pressure sensor 30 may be disposed on lead 12, and lead 12 may be implanted in interventricular septum 34. Lead 12 may include more or fewer electrodes and/or pressure sensors than are depicted in FIG. 6. In general, pacemaker 162 may sense electrical activity and may pace heart 20 via atrial electrode 26, right ventricular electrode 28 and left ventricular electrode 38. Pacemaker 162 may monitor the heart rate of the patient continuously by observing signals sensed via electrodes 26, 28 and 38 and/or by regulating paces delivered via electrodes 28 and 38.

System 160 may include a pressure monitor 164, which is also coupled to lead 12. In general, pressure monitor 164 receives pressure signals from pressure sensor 30. Sensor 30 may generate pressure signals itself or may modulate pressure signals conducted through lead 12. The pressure signals are a function of the fluid pressure at the site where pressure sensor 30 is disposed. In an embodiment of the invention shown in FIG. 3, pressure sensor 30 is disposed in right ventricle 24 of heart 20. Pressure monitor 164 receives, monitors and analyzes the pressure signals, as will be described in more detail below. An example of pressure monitor 164 is the Chronicle™ Implantable Hemodynamic Monitor manufactured by and commercially available from Medtronic, Inc. of Minneapolis, Minn.

System 160 may include one or more additional monitors 166 that receive signals from one or more additional sensors 168. Additional monitor 166 and sensor 168 detect and/or collect other physiological data. An example of an additional sensor 168 may be activity sensor 44 shown in FIG. 4. A temperature sensor and an oxygen sensor may be other examples of additional sensor 168.

In FIG. 6, additional sensor 168 is coupled to a distinct lead 170. In some embodiments of the invention, one or more additional sensors 168 may be coupled to lead 12. In other embodiments of the invention, pacing and/or sensing electrodes 26, 28, 38, pressure sensor 30 and additional sensors 168 may be coupled to different leads, and the invention is not restricted to any particular number of leads. Nor is the invention restricted to particular placements of leads. Although implantation of a single lead 12 in septum 34 is advantageous in many respects, the invention encompasses sensors placed endocardially and epicardially.

Pacemaker 162, pressure monitor 164 and additional monitor 166 are coupled to processor 172. Processor 172 is associated with memory 174. Processor 172 is shown as logically separate from pacemaker 162, pressure monitor 164 and monitor 166, but in practice processor 172 may be housed inside pacemaker 162, or inside pressure monitor 164, or inside monitor 166 or may be distributed among pacemaker 162, pressure monitor 164, or monitor 166.

Processor 172 may, for example, be included in microprocessor 128 and/or pacer timing/control circuitry 140 in the embodiment of implanted medical device 10 shown in FIG. 5, for example. Alternatively, some processing functions may be preformed in one device and other processing functions may be preformed in another device. In another alternative, processor 172 may be physically separate from pacemaker 162, pressure monitor 164 and monitor 166. Moreover, pacemaker 162, pressure monitor 164, monitor 166 and processor 172 may be realized as a single implantable device. The invention encompasses all of these variations.

Data collected by pacemaker 162, pressure monitor 164, monitor 166 and/or processor 172 may be retrieved via input/output devices such as remote distribution link 176 or RF telemetry 178. Further, pacemaker 162, pressure monitor 164, monitor 166 and/or processor 172 may receive information such as data or programming instructions via input/output devices 176, 178. Remote distribution link 176 may provide a channel for uploading or downloading information over a telephone line or over the internet, for example. RF telemetry 178 may communicate information on a dedicated wireless channel. Typically, a patient is required to visit an office of a physician when information is to be uploaded or downloaded via RF telemetry 178.

Processor 172 may collect raw data detected by sensors 26, 28, 30, 38 and 168. The data may relate to electrical activity, pressure, temperature, patient activity and the like. Processor 172 may also process the raw data to obtain additional useful information. One example of data processing is rhythm discrimination, which will be discussed in more detail below. Further, processor 172 may organize raw and/or processed data according to various parameters, as will be described below.

Processor 172 may be configured to discriminate between or among various heart rhythms and classify the rhythms. When processor 172 detects a possible tachyarrhythmia, for example, processor 172 performs computations to classify the tachyarrhythmia. Classifying the tachyarrhythmia may include identifying or discriminating the form of tachyarrhythmia, such as non-sustained ventricular tachycardia or sustained ventricular tachycardia. Some forms of tachyarrhythmia are life-threatening, while other forms of tachyarrhythmia pose little risk to the life of the patient. When the implanted device identifies a life-threatening tachyarrhythmia, the implanted device may provide therapy to the heart, such as anti-tachycardia pacing, cardioversion or defibrillation.

Classifying the tachyarrhythmia involves applying powerful discriminatory algorithms. In general, signals from electrodes 26, 28 and/or 38 are subjected to digital signal analysis. One technique for preparing signals for digital signal analysis is described above in connection with FIG. 5. In particular, switch matrix 124 may be used to select which of the signals will be analyzed, and analog signals may be converted to digital signals with A/D converter 134.

Processor 172 may include a specialized module for classification, such as a PR Logic™ module, manufactured by and commercially available from Medtronic Inc. of Minneapolis, Minn. Several pacing systems may include a PR Logic module, such as AT-500 pacemakers, or InSync-ICD or Gem DR implantable pacemaker-cardioverter-defibrillators, manufactured by and commercially available from Medtronic, Inc. of Minneapolis, Minn. A PR Logic module receives atrial and ventricular electrical signals, and integrates rate detection data with information about conduction patterns, regularity and AV dissociation. The PR Logic module maintains a high sensitivity for ventricular arrhythmia, and also discriminates ventricular arrhythmia from atrial arrhythmia such as supraventricular tachycardia (SVT).

The invention combines classification of rhythm with collection of other data, such as pressure data. Pressure monitor 164, for example, may receive pressure data from pressure sensor 30, but may not receive other data that may be pertinent to the conditions that generated the data. For example, pressure data collected during unpaced, normal sinus rhythm may be different from pressure data collected during a premature ventricular contraction (PVC), or during a ventricular tachycardia (VT) episode, or during an SVT episode, or during atrio-biventricular pacing, or during atrial fibrillation, with or without pacing. Moreover, the differences between pressure data taken under different conditions may have clinical significance to the patient's physician.

Figure 7:
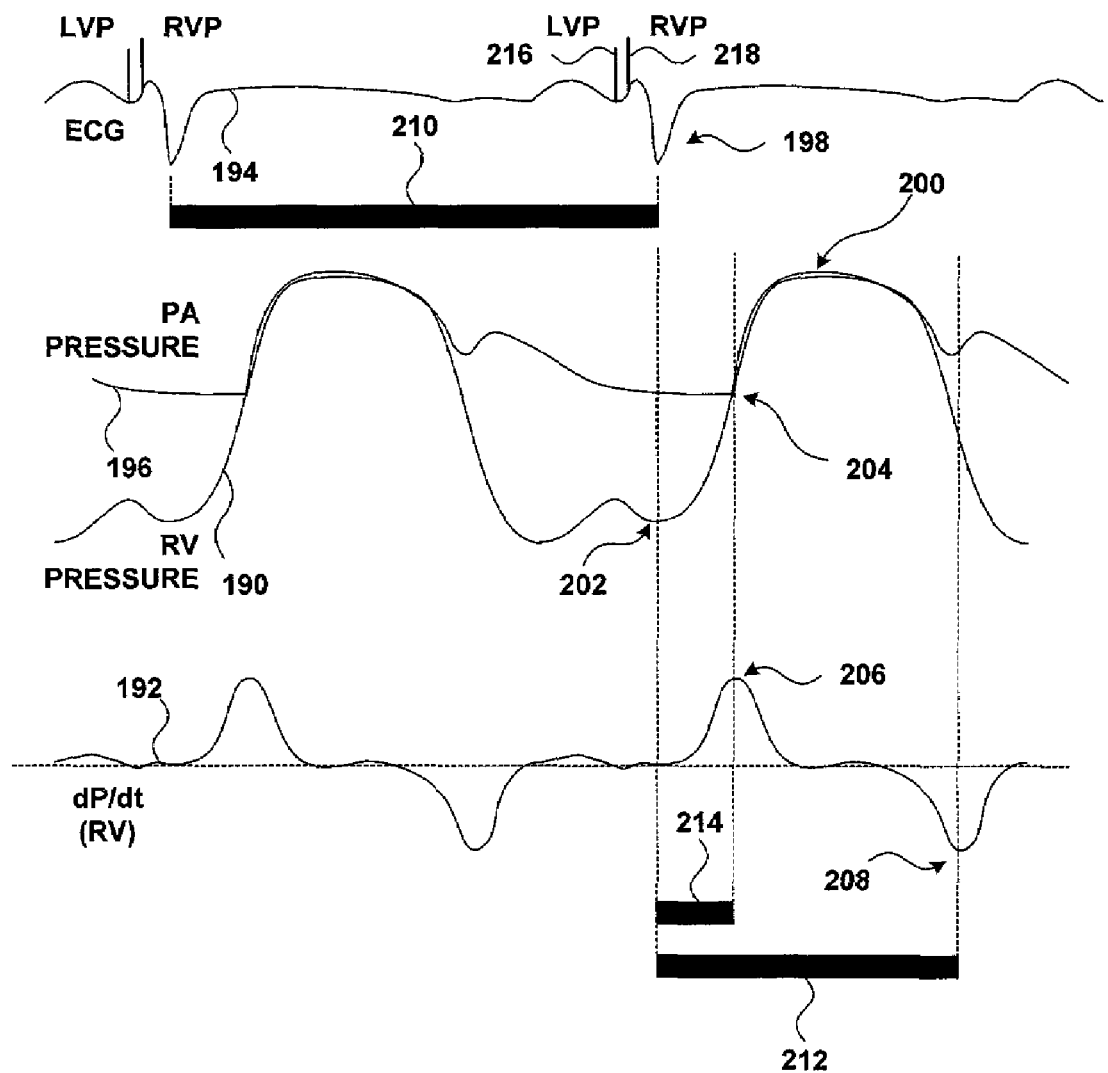
FIG. 7 is a timing diagram showing an electrocardiogram signal, a corresponding right ventricular pressure signal and a derivative of the right ventricular pressure signal, and illustrating measurement of exemplary parameters

FIG. 7 illustrates some kinds of data that may be sensed by pressure sensor 30 and received by pressure monitor 164. These data may have clinical significance for some patients. FIG. 7 is a timing diagram showing a right ventricular pressure 190 and a corresponding derivative 192 of the right ventricular pressure 190 with respect to time, denoted dP/dt (RV). Right ventricular pressure curve 190 reflects the blood pressure in right ventricle 24, which is where pressure sensor 30 may be located, as shown in FIGS. 2 and 3. Derivative curve 192 in FIG. 7 may be obtained from the same pressure data used to generate right ventricular pressure curve 190. Derivative curve 192 may be generated using analog or digital techniques, and may be generated by pressure monitor 164, processor 172 or both.

FIG. 7 further shows for purposes of reference an electrocardiogram (ECG) signal 194 and pulmonary artery pressure 196. ECG 194 and pulmonary artery pressure 196 may be sensed by a sensor other than pressure sensor 30 in right ventricle 24. ECG 194 may be sensed by, for example, an electrode on an external electrocardiograph, and pulmonary artery pressure 196 may be sensed by a pressure sensor in a pulmonary artery. Some features of ECG signal 194, such as R-wave 198, may be sensed with implanted electrodes such as ventricular electrodes 28 and 38.

Many quantities of clinical interest may be measured, observed or derived from the data shown in FIG. 7. For example, the right ventricular systolic pressure may be measured by observing the peak pressure 200 in right ventricle 24, and the right ventricular diastolic pressure may be measured by observing the pre-systolic low pressure 202 in right ventricle 24. Pulse pressure may be derived from right ventricular systolic pressure and right ventricular diastolic pressure, because pulse pressure represents the difference in the quantities.

The right ventricular mean pressure is another pressure of clinical significance. The right ventricular mean pressure represents the mean pressure in right ventricle 24 during a cardiac cycle. The right ventricular mean pressure may be computed by computing the mean of right ventricular pressure curve 190 over a cardiac cycle.

Another pressure of clinical significance is the estimated pulmonary artery diastolic pressure (ePAD) 204. ePAD 204 is a significant pressure because ePAD closely reflects the pulmonary capillary wedge pressure, which reflects the average pressure in the left atrium over a cardiac cycle, also called the mean left atrial pressure. In addition, ePAD 204 reflects the filling pressure in left ventricle 36 during diastole, also called the left ventricular end diastolic pressure.

ePAD 204 may be measured by finding the pressure on right ventricular pressure curve 190 that drives open the pulmonary valve. When right ventricle 24 activates and begins to contract, no blood leaves right ventricle 24 for a short period, and the contraction of right ventricle 24 is isovolumetric. During isovolumetric contraction, the right atrioventricular valve of heart 20 is closed by backward pressure differential forces. The pulmonary valve is likewise closed, as the pressure in right ventricle 24 is insufficient to force blood through the pulmonary valve. Pressure in right ventricle 24 rises until the pressure overcomes the pressure in the pulmonary arteries, as reflected in pulmonary artery pressure curve 196, driving the pulmonary valve open, and ejecting blood from right ventricle 24 into the pulmonary arteries. When the pulmonary valve opens, contraction is no longer isovolumetric. Pressure in right ventricle 24, although still increasing due to ventricular contraction, increases at a slower rate. As a result, there is an inflection point in right ventricular pressure curve 190 when the pulmonary valve opens, representing the point of maximum change of pressure with time. In right ventricular pressure curve 190, the inflection point is the point of maximum slope.

The right ventricular pressure at this inflection point is ePAD 204. The inflection point may be found by reference to dP/dt (RV) curve 192. Because the slope of right ventricular pressure curve 190 is at its maximum at the inflection point, dP/dt (RV) curve 192 peaks 206 at the same time the inflection point occurs.

The maximum 206 of dP/dt (RV) curve, also called +dpdt, may be of clinical significance in its own right. The minimum 208 of dP/dt (RV) curve, also called –dPdt, may also be of clinical significance. –dP/dt 208 occurs when ventricular ejection concludes and isovolumetric relaxation begins. In other words, –dP/dt 208 signals the completion of the ventricular systolic phase and the beginning of the ventricular diastolic phase.

Many time intervals may be measured using the data in FIG. 7. The duration of a cardiac cycle 210 may be measured between successive R-waves 198. This duration is also called the R—R interval. R—R interval 210 is inversely related to heart rate. Another interval of clinical significance is the systolic time interval (STI) 212 which represents the time between sensing R-wave 198 and –dP/dt 208, i.e., the completion of the ventricular systolic phase. The interval between sensing R-wave 198 and +dP/dt 206, which signals the opening of the pulmonary valve and the commencement of ejection into the pulmonary arteries, is the pre-ejection interval (PEI) 214, another interval of clinical significance.

The data shown in FIG. 7 do not result from an intrinsic, normal sinus rhythm of heart 20. Rather, ECG signal 194 shows that the patient received bi-ventricular pacing. On each cardiac cycle shown in FIG. 7, the patient received a left ventricular pace 216 from left ventricular electrode 38, followed by a right ventricular pace 218 from right ventricular electrode 28. In general, the object of such bi-ventricular pacing is to synchronize the activation of ventricles 24, 36, and enhance the hemodynamic performance of heart 20.

The quantities that may be observed or derived from the data in FIG. 7, such as right ventricular systolic pressure, ePAD or PEI, may be markedly different under different conditions. When heart 20 beats intrinsically, for example, the quantities of significance may be quite different form the same quantities measured during bi-ventricular pacing. Indeed, the patient's physician may compare observations and measurements made during intrinsic beats with observations and measurements made during bi-ventricular pacing, and may determine what pacing regimen, if any, is best suited to the patient. Other conditions that may affect measurements and observations may include various arrhythmias, such as SVT's, PVC's, ventricular tachycardia (VT) or paroxysmal atrial fibrillation (PAF), to name a few.

FIG. 8 is a chart 230 that illustrates a technique for recording data as a function of cardiac rhythm type. Each of the columns 232 represents a type of cardiac rhythm, such as unpaced sinus rhythm, bi-ventricular paced rhythm in a pacing mode such as VDD, SVT, PVC, VT and PAF. During periods of rapid atrial arrhythmias, a mode switching function may take place, such as a switch from DDD mode to DDI mode, or from VDD mode to VVI mode. A response to PAF may be to pace in VVI or DDI modes, in which atrial sensing is deactivated and one or more ventricles are paced at a rate lower than the rate of atrial activation. Some cardiac rhythm types, such as SVT's and PVC's, may be detected and classified by processor 172 as described above.

Each of the rows 234 represents a parameter mentioned above. Some of the parameters, such as right ventricular systolic pressure, +dP/dt or ePAD, may be pressure-related. Other parameters, such as patient activity, patient temperature or oxygen saturation, may be observed via additional monitor 166 and sensor 168. Each cell 236 in the chart 230 relates a parameter to a cardiac rhythm type.

Each cell may be realized as a distinct register, address or set of addresses in memory 174. As data regarding parameters 234 are collected, the data may be stored according to the cardiac rhythm type 232. When the data are retrieved via input/output devices 176, 178, the patient's physician will be better able to understand how the cardiac rhythm types and the parameters are related.

The possible cardiac rhythm types 232 are merely for purposes of illustration, and the invention is not limited to collecting and storing data according to these particular cardiac rhythm types. Similarly, list of parameters 234 may be more or less extensive than is shown in FIG. 8.

Many of the parameters 234 may be collected on a beat-to-beat basis. The data may be stored on a beat-to-beat basis as well, but the invention is not limited to storage on a beat-to-beat basis. The data may also be summed, averaged, or otherwise processed to save memory 174 and to record short-term and/or long-term trends.

Figure 9:
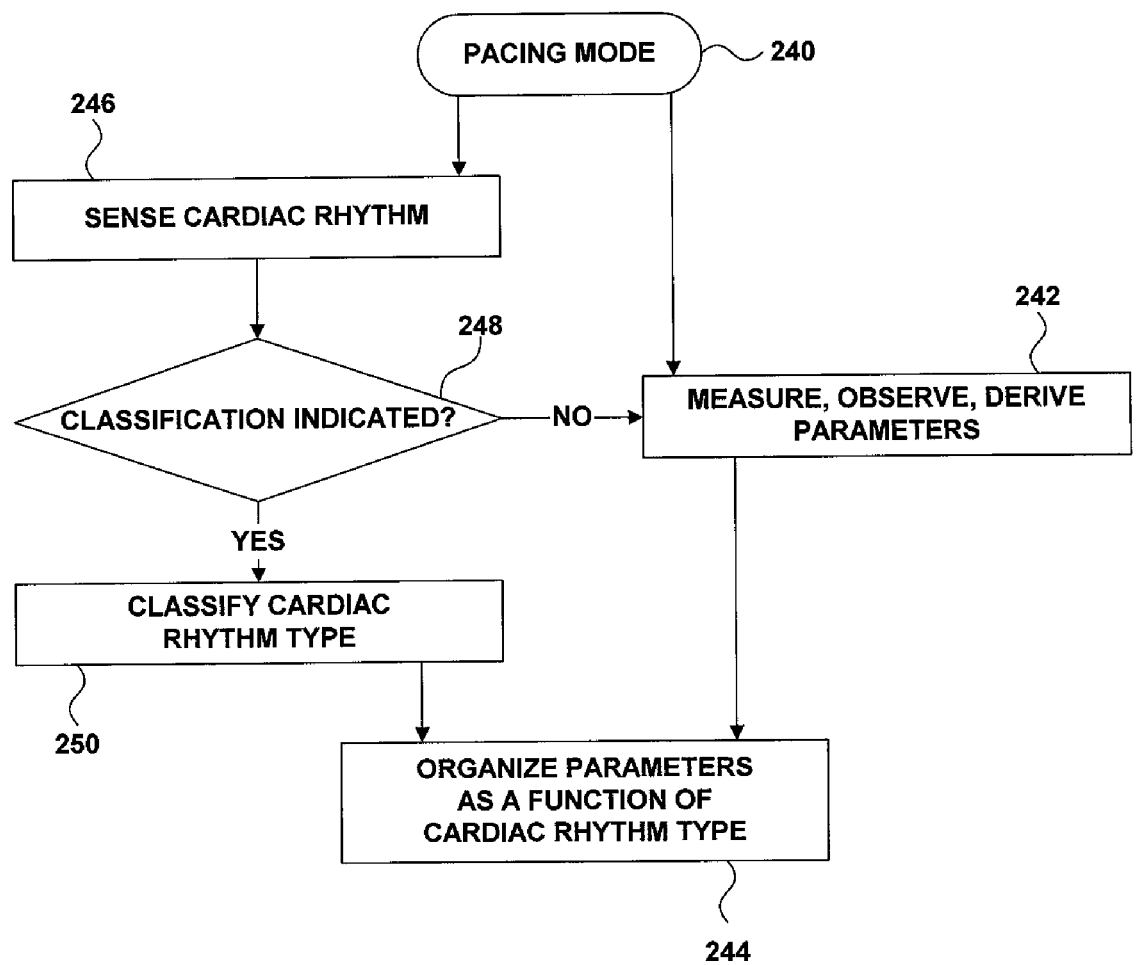
FIG. 9 is a flow diagram illustrating techniques for collection and organization of data.

FIG. 9 is a flow diagram that illustrates exemplary techniques for collecting data as a function of cardiac rhythm type. At the outset, processor 172 may be controlling pacemaker 162 to pace in a particular pacing mode (240). The pacing mode may be, for example, bi-ventricular pacing, or the pacing mode may be no pacing at all. Data may be collected for any of several parameters, such as parameters 234 shown in FIG. 8 (242). The data may then be stored as a function of cardiac rhythm type (244). In some cases, the cardiac rhythm type is a function of the pacing mode.

On every cardiac cycle, the cardiac rhythm may be sensed to some degree (246). In some circumstances, there is no indication that the patient may be experiencing an arrhythmia, so no classification computations are indicated (248). In other circumstances, however, the sensed cardiac rhythm suggests that the patient may be experiencing an arrhythmia (248), and processor 172 classifies the arrhythmia. When an arrhythmia is detected and classified, the data may then be stored as a function of the arrhythmia (244).

The invention may offer several advantages. One of the advantages is enhanced monitoring of the status of the patient. In particular, the patient's physician may be better able to monitor how the parameters are related to the various cardiac rhythm types. As a result, the patient's physician may be better able to assess the effectiveness of the patient's therapy, and may design new therapies customized to the needs of the patient.

Furthermore, storing the data as a function of cardiac rhythm type prevents commingling of data that may give a distorted picture of the patient's condition. For example, storing the data as a function of cardiac rhythm type prevents atypical measurements, which may be caused by atypical cardiac rhythms, from being commingled with data that are more typical. The patient's physician may be interested in seeing data pertaining to atypical cardiac rhythms, for example, but inclusion of data from typical cardiac rhythms may distort the data of interest. By storing the data as a function of cardiac rhythm type, the data for each cardiac rhythm type are kept separate, and distortion of data is less likely to occur.

Although the invention is not limited to implementation with a single lead, use of a single lead may have many advantages. In particular, the task of implanting the various sensors can be simplified when the sensors are coupled to a single lead. In the case of bi-ventricular pacing, it may be easier and more effective to implant an intra-septal lead having right and left ventricular electrodes than to implant the electrodes on separate leads. Implanting a single lead may take less time than implanting multiple leads. Implanting a single lead may also involve placing less material in the patient than implanting multiple leads.

In addition, the invention can be adapted to a variety of devices. Although the invention was described in connection with a single lead that can perform bi-ventricular pacing, the invention can be adapted to a variety of one- two- three- and four-chamber devices. The invention can be adapted to any configuration of electrode placements and is not limited to the electrode placements depicted in FIGS. 1–3.

The preceding specific embodiments are illustrative of the practice of the invention. It is to be understood, therefore, that other expedients known to those skilled in the art or disclosed herein may be employed without departing from the invention or the scope of the claims. For example, the data collected by the invention may be used to automatically control therapy for the patient. By monitoring ePAD, for example, processor 172 may be able to determine whether right ventricular pressures are becoming too high. In response to detection of elevated ePAD, processor 172 may, for example, change pacing therapies provided by pacemaker 162. Processor 172 my also control another device, such as implanted drug pump, to deliver medicine in response to the elevated ePAD measurements.

The invention further includes within its scope the methods of making and using the systems described above. These methods are not limited to the specific examples described above, but may be adapted to meet the needs of a particular patient. The invention also includes within its scope any of computer-readable media comprising instructions for causing a programmable processor, such as microprocessor, to carry out the techniques described above. Such computer-readable media include, but are not limited to, magnetic and optical storage media, and read-only memory such as erasable programmable read-only memory or flash memory accessible by the processor. The media may be included in a programmer, for example, or in read-only memory accessible by an implanted processor. These and other embodiments are within the scope of the following claims.

In the claims, means-plus-functions clauses are intended to cover the recited structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

The invention claimed is:

1. A device comprising:
 a monitor that monitors a cardiac parameter;
 a processor that classifies a cardiac rhythm type; and
 memory that stores the cardiac parameter as a function of the cardiac rhythm type, wherein the monitor comprises a temperature monitor.

2. The device of one of claim 1, wherein the monitor further comprises an activity monitor.

3. The device of claim 2, wherein the processor classifies the cardiac rhythm type as at feast one of normal sinus rhythm, paced ventricular rhythm, supraventricular tachycardia, premature ventricular contraction, ventricular tachycardia and atrial fibrillation.

4. A device comprising:
 a monitor that monitors a cardiac parameter;
 a processor that classifies a cardiac rhythm type;
 memory adapted to store the cardiac parameter as a function of the cardiac rhythm type
 a first electrode disposed in a left ventricle;
 a second electrode disposed in a right ventricle; and
 a pressure sensor disposed in one of the left ventricle and the right ventricle.

5. The device of claim 4. further comprising a third electrode disposed in a right atrium.

6. A device comprising:
 a monitor that monitors a cardiac parameter;
 a processor that classifies a cardiac rhythm type;
 memory adapted to store the cardiac parameter as a function of the cardiac rhythm type
 a first electrode;
 a second electrode;
 a pressure sensor; and
 a single lead, wherein the first electrode, the second electrode and the pressure sensor are deployed on the lead, wherein the single lead is disposed in one of a left and a right ventricle.

7. The device of claim 6, further comprising a third electrode deployed on the lead.

8. A device comprising:
a monitor that monitors a cardiac parameter;
a processor that classifies a cardiac rhythm type; and
memory that stores the cardiac parameter as a function of the cardiac rhythm type, wherein the memory comprises a plurality of registers, and wherein each register stores data pertaining to a cardiac parameter and a cardiac rhythm type.

9. The device of claim 8, further comprising a pulse generator means for delivering a cardiac pacing therapy.

10. The device of claim 9, wherein the pulse generator delivers a first pacing pulse to a first ventricle and a second pacing pulse to a second ventricle.

11. The device of claim 9, wherein the processor controls the pulse generator as a function of a cardiac parameter stored in memory.

12. The device of claim 9, wherein the device comprises an implantable medical device and the monitor, processor, memory, and pulse generator means are disposed within a single biocompatible enclosure.

* * * * *

UNITED STATES PATENT AND TRADEMARK OFFICE
CERTIFICATE OF CORRECTION

| | | |
|---|---|---|
| PATENT NO. | : 7,058,450 B2 | Page 1 of 1 |
| APPLICATION NO. | : 10/126816 | |
| DATED | : June 6, 2006 | |
| INVENTOR(S) | : Chester Struble et al. | |

It is certified that error appears in the above-identified patent and that said Letters Patent is hereby corrected as shown below:

Column 18, line 38, please delete "feast" and insert --least--

Signed and Sealed this

Fifteenth Day of May, 2007

JON W. DUDAS
*Director of the United States Patent and Trademark Office*